United States Patent
Deshpande

(10) Patent No.: US 8,422,002 B2
(45) Date of Patent: Apr. 16, 2013

(54) MALARIA DETECTION BY SMALL ANGLE LIGHT SCATTERING

(76) Inventor: Satish Deshpande, Guelph (CA)

( * ) Notice: Subject to any disclaimer, the term of this patent is extended or adjusted under 35 U.S.C. 154(b) by 201 days.

(21) Appl. No.: 12/999,119

(22) PCT Filed: Jun. 24, 2009

(86) PCT No.: PCT/US2009/048356
§ 371 (c)(1),
(2), (4) Date: Dec. 15, 2010

(87) PCT Pub. No.: WO2010/008870
PCT Pub. Date: Jan. 21, 2010

(65) Prior Publication Data
US 2011/0102769 A1    May 5, 2011

Related U.S. Application Data

(60) Provisional application No. 61/132,925, filed on Jun. 24, 2008.

(51) Int. Cl.
*G01N 33/48*    (2006.01)

(52) U.S. Cl.
USPC .............................................. 356/39; 356/40

(58) Field of Classification Search ............... 356/39–41
See application file for complete search history.

(56) References Cited

U.S. PATENT DOCUMENTS

| | | | |
|---|---|---|---|
| 2002/0164810 A1* | 11/2002 | Dukor et al. ................... | 436/64 |
| 2004/0246479 A1* | 12/2004 | Cartlidge et al. ............. | 356/335 |
| 2005/0105077 A1* | 5/2005 | Padmanabhan et al. ........ | 356/39 |
| 2008/0212069 A1* | 9/2008 | Goldberg et al. ............... | 356/36 |

* cited by examiner

*Primary Examiner* — Michael P Stafira
(74) *Attorney, Agent, or Firm* — Carol Lynn Barnes

(57) ABSTRACT

Differences between a control profile of light scattered by a control sample from a sample of whole blood and a detection profile of light scattered from a detection sample from the sample of whole blood with a detection agent added indicate malaria infection of the whole blood, where the light scattering is Mie scattering by an ensemble of scatterers in samples which are detection optimized to a concentration just low enough so that each scatterer which does scatter light scatters light only once, where the profiles are for light scattered between zero and five degrees.

8 Claims, 2 Drawing Sheets

MALARIA DETECTION BY SMALL ANGLE LIGHT SCATTERING

CROSS-REFERENCE TO RELATED APPLICATIONS

This application claims priority of U.S. provisional application 61/132,925 filed 24 Jun. 2008 which is incorporated herein by reference.

DETAILED DESCRIPTION

Figure 1:
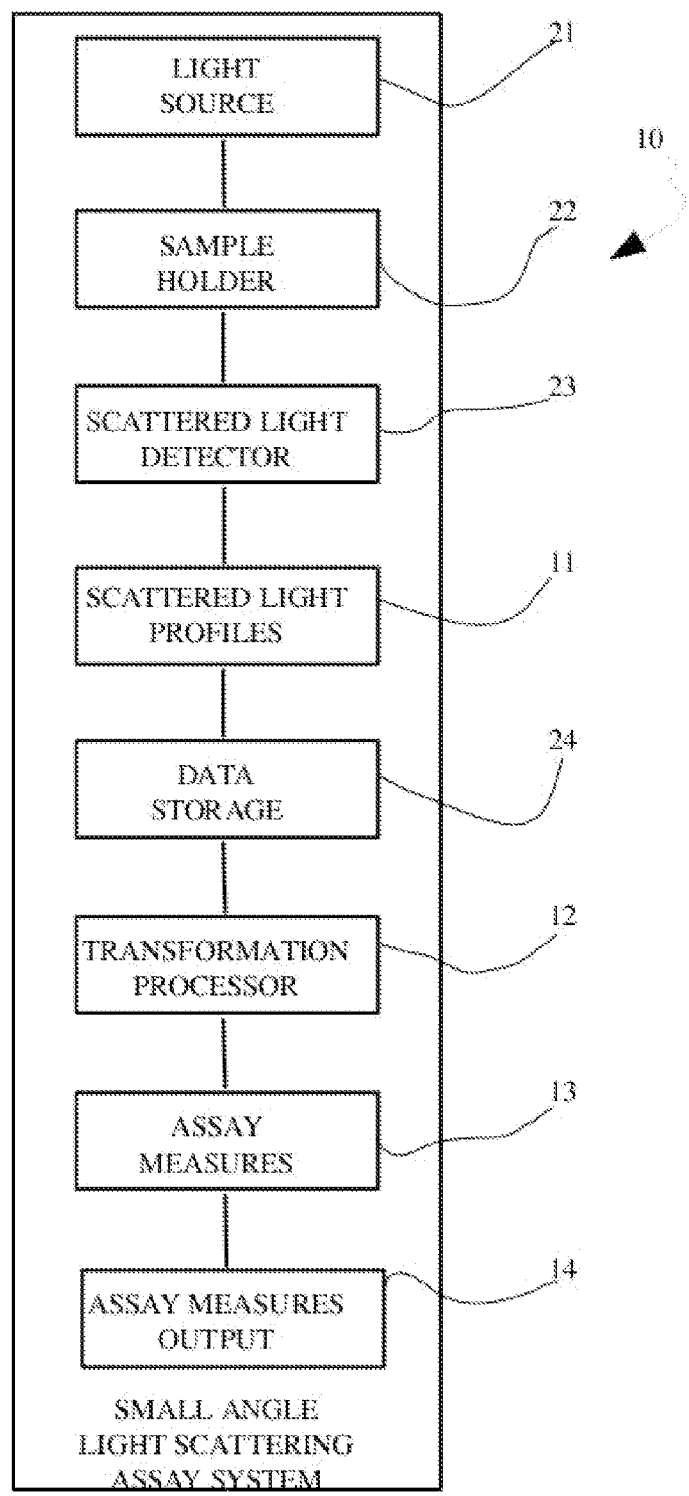
FIG. 1 is a schematic representation of the system 10.

Light scattering profiles—each light scattering profile representing an angular distribution of scattered light intensity over an angular range including at least a first region of interest between zero degrees and five degrees away from the central ray—are transformed by the system to assay measures of malaria infection.

The transformation uses changes between a control profile and a detection profile to determine assay measures.

Unexpected discovery of this transformation, which is not affected by long-troubling observer specificity, makes possible the long-sought goal of easy and rapid detection of malaria infection early enough for effective treatment. Parasitemia as low as 0.0001 percent has been measured, and lower may be possible.

The small angle light scattering system for detecting malaria infection operates a small angle light scattering method for detecting malaria infection.

Light from a light source 21 is incident on a sample in a sample holder 22. The sample alternatively comprises a whole blood sample, a control sample from the whole blood sample, and a first detection sample from the whole blood sample with a first detection agent added.

Light scattered by cells in the sample is incident on a scattered light detector 23. Light scattering profiles 11 are output from the scattered light detector and input to data storage 24. A transformation processor 12 determines changes between light scattering profiles and outputs assay measures 13 which are output by the assays measures output component 14 of the system.

Figure 2:
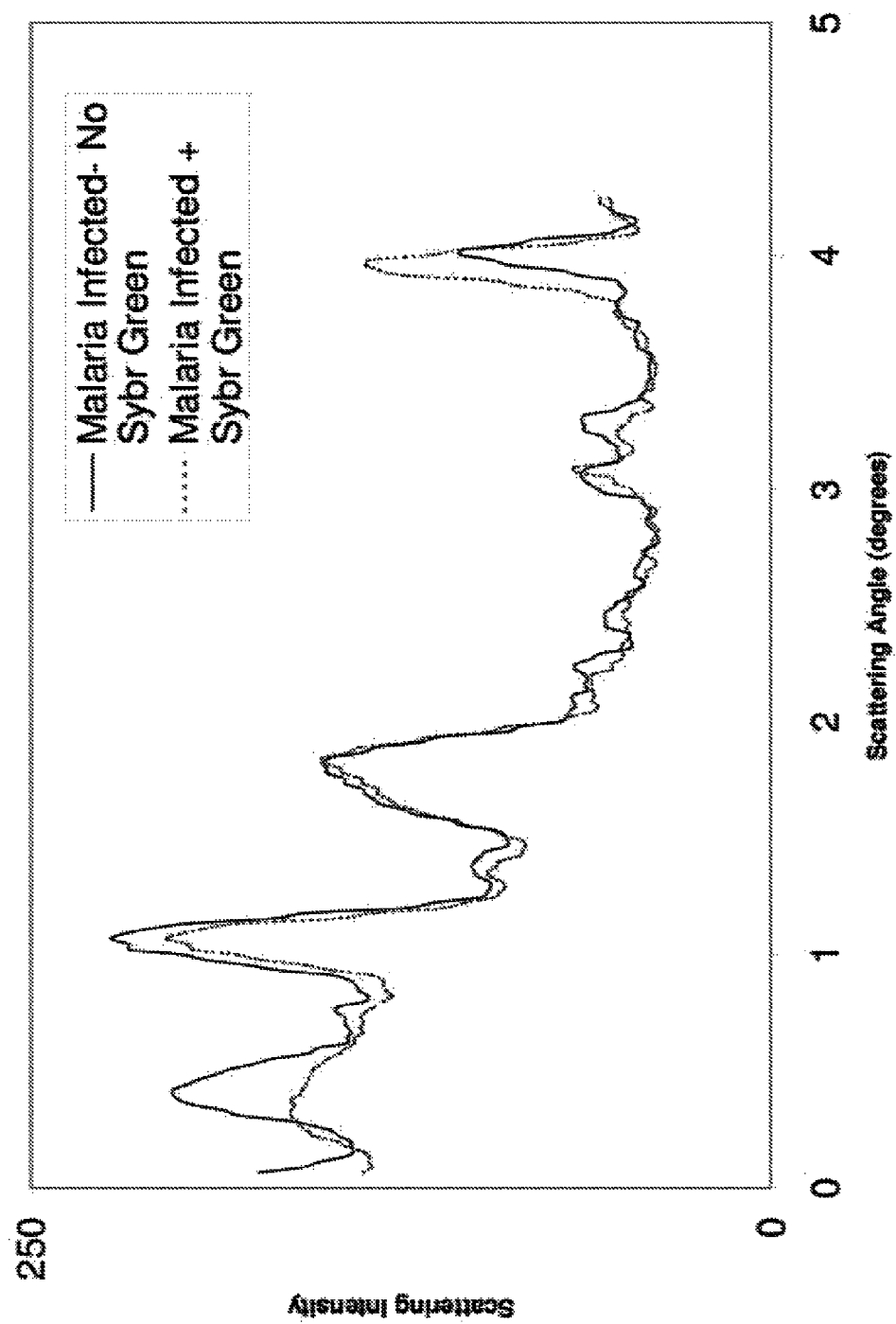
FIG. 2 shows comparison of a control profile and a detection profile for malaria infected blood.

FIG. 2 shows a control profile (solid curve) and a detection profile (dotted curve). The detection agent here is SYBR Green. The changes between the two curves is measurably greater than random variations among profile measurements.

Similar curves obtain for other detection agents such as riboflavin and pentamidine. A detection agent can be any agent which reliably produces changes between control and detection profiles greater than random changes when blood is malaria infected.

One transformation to measure the changes is to sum the absolute values of the intensity differences for each pixel, which is the net area between the two curves. Any other means for measuring the changes, which reliably distinguishes between changes caused by the detection agent and random variations can be used.

The light scattering is Mie scattering by an ensemble of scatterers in the sample which is detection optimized to a concentration just low enough so that each scatterer which does scatter light scatters light only once. Light scattered by cells at the smallest angles away from the central ray of the light source can be blocked.

Light scattered at angles up to five degrees away from the central ray is superposition of scattering by whole cells and parts of cells. This superposition of scatterings includes also superposition of various orders of Mie scatterings. These superpositions result in profiles with one and more peaks. If scatterers in samples have some long range order, then this long range order can also contribute to the profile structure akin to scattering by a lattice.

It is unnecessary to know the source of the structure of profiles. Information about malaria infection is manifest in changes between control and detection profiles. Changes between profiles can be caused by changes in size and shape of scatterers and can be caused by changes in index of refraction of scatterers and of the medium and can be changed by loss of scatterers.

When blood in samples is malaria infected, changes between a control profile and a detection profile are measurably greater than random changes among profiles as can be seen in FIG. 2.

To isolate changes which indicate malarial infection from other changes, a calibration transformation is applied. A calibration transformation has been applied to the curves in FIG. 2.

The small angle light scattering assay system for detecting malaria infection comprises a light source having a central ray, a sample holder for holding a sample, a scattered light detector, a data storage component, and a transformation processor.

The sample is detection optimized.

The sample alternatively comprises: a whole blood sample, a control sample from the whole blood sample, and a first detection sample from the whole blood sample with a first detection agent added.

The scattered light detector outputs light scattering profiles. The light scattering is Mie scattering by an ensemble of scatterers in the sample which is detection optimized to a concentration just low enough so that each scatterer which does scatter light scatters light only once.

Each light scattering profile comprises measured values of scattered light intensity at each pixel Pd of the scattered light detector in at least a first detection region of interest between zero degrees and five degrees away from the central ray, each pixel being proportional to an angle away from the central ray.

The profiles comprise:

A detection profile comprising measured detection sample values DI(Pd) of scattered light intensity at each scattered light detector pixel Pd in the first detection region of interest when the sample is the detection sample, and A control profile comprising measured control sample values CI(Pd) of scattered light intensity at each scattered light detector pixel Pd in the first detection region of interest when the sample is the control sample.

Light scattering profiles output from the scattered light detector are input to the data storage component.

The transformation processor transforms profiles stored in the data storage component to assay measures. A first assay measure results from determination of first assay differences between the first detection profile and the control profile.

When first assay differences are not greater than random measurement variations, then the first assay measure comprises a report of no malaria infection of the sample.

When first assay differences are greater than random measurement variations, then the first assay measure comprises a report of malaria infection of the sample.

The first assay measure can be any assay member of an assay plurality of assay measurements.

There are many ways that control profiles and detection profiles can be compared. Any comparison which are reliably sensitive to differences indicating malarial infection can be used.

An assay member of the assay plurality can comprise:

A transformation $A=\Sigma|DI(Pd)\times M-CI(Pd)|$, summing over all pixels Pd in the first detection region of interest, where M is:

A calibration transformation $M=\Sigma DI(Pc)/\Sigma CI(Pc)$, summing over all pixels Pc in a first calibration region of interest.

The DI(Pc) are measured detection sample values of scattered light intensity at each scattered light detector pixel Pc in the first calibration region of interest when the sample is the detection sample.

The CI(Pc) are measured control sample values of scattered light intensity at each scattered light detector pixel Pc in the in the first calibration region of interest when the sample is the control sampler.

The first calibration region of interest is a constant-angle region of interest chosen by reference to historical data to be used to isolate infection indicating changes from other changes when the whole blood sample is malaria infected blood.

The first detection agent can be any detection member of a detection plurality of detection agents.

The first region of interest can be any region member of a region plurality of regions of interest.

The first calibration region of interest can be any calibration member of a calibration plurality of calibration regions of interest.

The system operates a small angle light scattering assay method for detecting malaria infection. The method comprises obtaining from a sample small angle light scattering profiles and transforming profiles to assay measures.

The sample is detection optimized. The sample alternatively comprises: a whole blood sample, a control sample from the whole blood sample, and a first detection sample from the whole blood sample with a first detection agent added.

The light scattering is Mie scattering by an ensemble of scatterers in the sample which is detection optimized to a concentration just low enough so that each scatterer which does scatter light scatters light only once.

Each light scattering profile comprises measured values of scattered light intensity at each pixel Pd of a scattered light detector in at least a first detection region of interest between zero degrees and five degrees away from a central ray of a light source incident on the sample, each pixel being proportional to an angle away from the central ray.

The profiles comprise:

A detection profile comprising measured detection sample values DI(Pd) of scattered light intensity at each scattered light detector pixel Pd in the first detection region of interest when the sample is the detection sample, and a control profile comprising measured control sample values CI(Pd) of scattered light intensity at each scattered light detector pixel Pd in the first detection region of interest when the sample is the control sample.

A first assay measure results from determination of first assay differences between the first detection profile and the control profile.

When first assay differences are not greater than random measurement variations, then the first assay measure comprises a report of no malaria infection of the sample.

When first assay differences are greater than random measurement variations, then the first assay measure comprises a report of malaria infection of the sample.

The first assay measure can be any assay member of an assay plurality of assay measurements.

An assay member of the assay plurality can comprise:

A transformation $A=\Sigma|DI(Pd)\times M-CI(Pd)|$, summing over all pixels Pd in the first detection region of interest, where M is:

A calibration transformation $M=\Sigma DI(Pc)/\Sigma CI(Pc)$, summing over all pixels Pc in a first calibration region of interest.

The DI(Pc) are measured detection sample values of scattered light intensity at each scattered light detector pixel Pc in the first calibration region of interest when the sample is the detection sample.

The CI(Pc) are measured control sample values of scattered light intensity at each scattered light detector pixel Pc in the in the first calibration region of interest when the sample is the control sampler.

The first calibration region of interest is a constant-angle region of interest chosen by reference to historical data to be used to isolate infection indicating changes from other changes.

The first detection agent can be any detection member of a detection plurality of detection agents.

The first region of interest is any region member of a region plurality of regions of interest.

The first calibration region of interest is any calibration member of a calibration plurality of calibration regions of interest.

The invention claimed is:

1. A small angle light scattering assay system for detecting malaria infection, the system comprising:
   a light source having a central ray;
   a sample holder for holding a sample,
   where the sample is detection optimized,
   where the sample alternatively comprises:
   a whole blood sample;
   a control sample from the whole blood sample; and
   a first detection sample from the whole blood sample with a first detection agent added;
   a scattered light detector,
   where the scattered light detector outputs light scattering profiles,
   where the light scattering is Mie scattering by an ensemble of scatterers in the sample which is detection optimized to a concentration just low enough so that each scatterer which does scatter light scatters light only once,
   where each light scattering profile comprises measured values of scattered light intensity at each pixel Pd of the scattered light detector in at least a first detection region of interest between zero degrees and five degrees away from the central ray, each pixel being proportional to an angle away from the central ray,
   where the profiles comprise:
   a detection profile comprising measured detection sample values DI(Pd) of scattered light intensity at each scattered light detector pixel Pd in the first detection region of interest when the sample is the detection sample, and
   a control profile comprising measured control sample values CI(Pd) of scattered light intensity at each scattered light detector pixel Pd in the first detection region of interest when the sample is the control sample;
   a data storage component,
   light scattering profiles output from the scattered light detector being input to the data storage component;

a transformation processor for transforming profiles stored in the data storage component to assay measures, where a first assay measure results from determination of first assay differences between the first detection profile and the control profile, where, when first assay differences are not greater than random measurement variations, then the first assay measure comprises a report of no malaria infection of the sample, where, when first assay differences are greater than random measurement variations, then the first assay measure comprises a report of malaria infection of the sample.

2. The system of claim 1 where the first assay measure is any assay member of an assay plurality of assay measurements.

3. The system of claim 2 where an assay member of the assay plurality comprises:

a transformation $A=\Sigma|DI(Pd) \times M-CI(Pd)|$, summing over all pixels Pd in the first detection region of interest, where M is a calibration transformation $M=\Sigma DI(Pc)/\Sigma CI(Pc)$, summing over all pixels Pc in a first calibration region of interest, where DI(Pc) are measured detection sample values of scattered light intensity at each scattered light detector pixel Pc in the first calibration region of interest when the sample is the detection sample, where CI(Pc) are measured control sample values of scattered light intensity at each scattered light detector pixel Pc in the in the first calibration region of interest when the sample is the control sampler, and where, the first calibration region of interest is a constant-angle region of interest chosen by reference to historical data to be used to isolate infection indicating changes from other changes.

4. The system of claim 1 where the first detection agent is any detection member of a detection plurality of detection agents.

5. The system of claim 1 where the first region of interest is any region member of a region plurality of regions of interest.

6. The system of claim 1 where the first calibration region of interest is any calibration member of a calibration plurality of calibration regions of interest.

7. A small angle light scattering assay system for detecting malaria infection, the system comprising:

a light source having a central ray;

a sample holder for holding a sample, where the sample is detection optimized, where the sample alternatively comprises:

a whole blood sample;

a control sample from the whole blood sample; and a first detection sample from the whole blood sample with a first detection agent added;

a scattered light detector, where the scattered light detector outputs light scattering profiles, where the light scattering is Mie scattering by an ensemble of scatterers in the sample which is detection optimized to a concentration just low enough so that each scatterer which does scatter light scatters light only once, where each light scattering profile comprises measured values of Mie scattered light intensity at each pixel Pd of the scattered light detector in at least a first detection region of interest between zero degrees and five degrees away from the central ray, each pixel being proportional to an angle away from the central ray, where the profiles comprise:

a detection profile comprising measured detection sample values DI(Pd) of scattered light intensity at each scattered light detector pixel Pd in the first detection region of interest when the sample is the detection sample, and a control profile comprising measured control sample values CI(Pd) of scattered light intensity at each scattered light detector pixel Pd in the first detection region of interest when the sample is the control sample;

a data storage component, light scattering profiles output from the scattered light detector being input to the data storage component;

a transformation processor for transforming profiles stored in the data storage component to assay measures, where a first assay measure results from determination of first assay differences between the first detection profile and the control profile, where, when first assay differences are not greater than random measurement variations, then the first assay measure comprises a report of no malaria infection of the sample, where, when first assay differences are greater than random measurement variations, then the first assay measure comprises a report of malaria infection of the sample, where the first assay measure is any assay member of an assay plurality of assay measurements, where an assay member of the assay plurality comprises:

a transformation $A=\Sigma|DI(Pd) \times M-CI(Pd)|$, summing over all pixels Pd in the first detection region of interest, where M is a calibration transformation $M=\Sigma DI(Pc)/\Sigma CI(Pc)$, summing over all pixels Pc in a first calibration region of interest, where DI(Pc) are measured detection sample values of scattered light intensity at each scattered light detector pixel Pc in the first calibration region of interest when the sample is the detection sample, where CI(Pc) are measured control sample values of scattered light intensity at each scattered light detector pixel Pc in the in the first calibration region of interest when the sample is the control sampler, where, the first calibration region of interest is a constant-angle region of interest chosen by reference to historical data to be used to isolate infection indicating changes from other changes, where the first detection agent is any detection member of a detection plurality of detection agents, where the first region of interest is any region member of a region plurality of regions of interest, and where the first calibration region of interest is any calibration member of a calibration plurality of calibration regions of interest.

8. A small angle light scattering assay method for detecting malaria infection, the method comprising:

obtaining from a sample small angle light scattering profiles, where the light scattering is Mie scattering by an ensemble of scatterers in the sample which is detection optimized to a concentration just low enough so that each scatterer which does scatter light scatters light only once, where the sample alternatively comprises:

a whole blood sample;

a control sample from the whole blood sample; and a first detection sample from the whole blood sample with a first detection agent added, where each light scattering profile comprises measured values of scattered light intensity at each pixel Pd of a scattered light detector in at least a first detection region of interest between zero degrees and five degrees away from a central ray of a light source incident on the sample, each pixel being proportional to an angle away from the central ray, where the profiles comprise:

a detection profile comprising measured detection sample values DI(Pd) of scattered light intensity at each scattered light detector pixel Pd in the first detection region of interest when the sample is the detection sample, and a control profile comprising measured control sample values CI(Pd) of scattered light intensity at each scattered light detector pixel Pd in the first detection region of interest when the sample is the control sample, transforming profiles to assay measures, where a first assay measure results from determination of first assay differences between the first detection profile and the control profile, where, when first assay differences are not greater than random measurement variations, then the first assay measure comprises a report of no malaria infection of the sample, where, when first assay differences are greater than random measurement variations, then the first assay measure comprises a report of malaria infection of the sample, where the first assay measure is any assay member of an assay plurality of assay measurements, where an assay member of the assay plurality comprises:

a transformation $A=\Sigma|DI(Pd)\times M-CI(Pd)|$, summing over all pixels Pd in the first detection region of interest, where M is a calibration transformation $M=\Sigma DI(Pc)/\Sigma CI(Pc)$, summing over all pixels Pc in a first calibration region of interest, where DI(Pc) are measured detection sample values of scattered light intensity at each scattered light detector pixel Pc in the first calibration region of interest when the sample is the detection sample, where CI(Pc) are measured control sample values of scattered light intensity at each scattered light detector pixel Pc in the in the first calibration region of interest when the sample is the control sampler, where, the first calibration region of interest is a constant-angle region of interest chosen by reference to historical data to be used to isolate infection indicating changes from other changes, where the first detection agent is any detection member of a detection plurality of detection agents, where the first region of interest is any region member of a region plurality of regions of interest, and where the first calibration region of interest is any calibration member of a calibration plurality of calibration regions of interest.

* * * * *